United States Patent
Rajagopal et al.

(10) Patent No.: US 11,950,887 B2
(45) Date of Patent: Apr. 9, 2024

(54) BLOOD PRESSURE MEASUREMENT APPARATUS AND METHODS OF USE THEREOF

(71) Applicant: California Institute of Technology, Pasadena, CA (US)

(72) Inventors: Aditya Rajagopal, Pasadena, CA (US); Dominic Yurk, Pasadena, CA (US); Yaser Abu-Mostafa, Pasadena, CA (US); Alaina Ann Brinley Rajagopal, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 270 days.

(21) Appl. No.: 17/020,740

(22) Filed: Sep. 14, 2020

(65) Prior Publication Data

US 2021/0076954 A1    Mar. 18, 2021

Related U.S. Application Data

(60) Provisional application No. 62/966,927, filed on Jan. 28, 2020, provisional application No. 62/900,125, filed on Sep. 13, 2019.

(51) Int. Cl.
*A61B 5/021* (2006.01)
*A61B 5/00* (2006.01)

(52) U.S. Cl.
CPC ........ *A61B 5/02133* (2013.01); *A61B 5/6832* (2013.01); *A61B 5/7405* (2013.01); *A61B 5/02141* (2013.01)

(58) Field of Classification Search
CPC ............ A61B 5/02108; A61B 5/02116; A61B 5/02125; A61B 5/02133; A61B 5/6832;
(Continued)

(56) References Cited

U.S. PATENT DOCUMENTS 4,015,092 A * 3/1977 Suzuki ............... G10H 1/18
200/283
4,771,792 A * 9/1988 Seale ............... A61B 5/205
702/56
(Continued)

FOREIGN PATENT DOCUMENTS

JP    2016007412 A    1/2016
JP      6373647 B2    8/2018
(Continued)

OTHER PUBLICATIONS

"Resonance." Merriam-Webster.com Dictionary, Merriam-Webster, https://www.merriam-webster.com/dictionary/resonance. Accessed Sep. 30, 2022 (Year: 2022).*
(Continued)

*Primary Examiner* — Devin B Henson
*Assistant Examiner* — Matthew Eric Ogles
(74) *Attorney, Agent, or Firm* — Sheppard Mullin Richter & Hampton LLP

(57) ABSTRACT

Some implementations of the disclosure describe a blood pressure measurement apparatus and method that enable continuous, non-invasive blood pressure measurement using sound and ultrasound transducers. In one implementation, a blood pressure measurement device includes: a first transducer configured to emit multiple soundwaves having multiple frequencies, the soundwaves configured to cause a blood vessel of a subject to vibrate; a second transducer configured to capture one or more ultrasound images of the blood vessel; and a processing device configured to: determine, based on the one or more ultrasound images, a wall thickness, a radius, and a resonant frequency of the blood vessel; and calculate, based on the wall thickness, the radius, and the resonant frequency, a blood pressure of the subject.

19 Claims, 7 Drawing Sheets

(58) Field of Classification Search
CPC ... A61B 5/7405; A61B 5/02141; A61B 5/021; A61B 5/6833; A61B 5/6831; A61B 5/683; A61B 5/7415; A61B 8/04; A61B 8/06
See application file for complete search history.

(56) References Cited

U.S. PATENT DOCUMENTS

| | | | | |
|---|---|---|---|---|
| 5,241,964 | A | * | 9/1993 | McQuilkin ........ A61B 5/02125 600/485 |
| 6,461,301 | B2 | | 8/2002 | Smith |
| 11,298,103 | B2 | * | 4/2022 | Weinberg ............. A61B 5/1075 |
| 2004/0211260 | A1 | | 10/2004 | Girmonsky et al. |
| 2006/0079782 | A1 | * | 4/2006 | Beach ................. G01S 7/52034 600/450 |
| 2011/0021924 | A1 | | 1/2011 | Sethuraman et al. |
| 2012/0116238 | A1 | | 5/2012 | Brand et al. |
| 2013/0197367 | A1 | | 8/2013 | Smok et al. |
| 2016/0345930 | A1 | | 12/2016 | Mizukami et al. |
| 2018/0209840 | A1 | | 7/2018 | Brand et al. |
| 2019/0008400 | A1 | * | 1/2019 | Richter ................ A61B 5/6876 |
| 2019/0200950 | A1 | * | 7/2019 | Brenner ................... A61B 8/04 |
| 2019/0313908 | A1 | | 10/2019 | Melodia et al. |

FOREIGN PATENT DOCUMENTS

JP         6385518 B2    9/2018
WO    WO-2019234767 A1 * 12/2019    .............. A61B 5/02

OTHER PUBLICATIONS

International Search Report and Written Opinion in PCT/US2020/050778, dated Dec. 24, 2020.
International Preliminary Report on Patentability for Application No. PCT/US2020/050778, dated Mar. 24, 2022, 8 pages.
PCT International Preliminary Report on Patentability dated Mar. 24, 2022, issued in related International Application No. PCT/US2020/050778 (8 pages).
PCT International Search Report and the Written Opinion dated Jun. 3, 2021, issued in related International Application No. PCT/US2021/015324 (10 pages).
PCT International Preliminary Report on Patentability dated Aug. 11, 2022, issued in related International Application No. PCT/US2021/015324 (7 pages).
Wang et al., "Monitoring of the central blood pressure waveform via a conformal ultrasonic device," Nature Biomedical Engineering, Sep. 2018, vol. 2, pp. 687-695.
Extended European Search Report dated Feb. 14, 2024, issued in related European Patent Application No. 21747357.8 (5 pages).

* cited by examiner

BLOOD PRESSURE MEASUREMENT APPARATUS AND METHODS OF USE THEREOF

CROSS-REFERENCE TO RELATED APPLICATIONS

This application claims priority to U.S. Provisional Application No. 62/966,927, titled "Blood Pressure Measurement Apparatus And Methods Of Use Thereof" and filed Jan. 28, 2020, and U.S. Provisional Application No. 62/900,125, titled "A Novel Method For Determining True Blood Pressure Using Resonant Modes Around The Circumference Of An Artery" and filed Sep. 13, 2019. Each of these applications is incorporated herein by reference in its entirety.

BACKGROUND

Blood pressure is an essential vital sign routinely used to manage patient care. During office visits, it is usually the first vital sign measured. During critical resuscitations in the emergency department, it is usually the primary vital sign used to determine quality of resuscitation, along with heart rate. These measurements in combination are indicators of shock, dehydration, hemorrhage, and provide one of the only quantitative methods of assessing the fluid resuscitation quality in patients requiring fluids. It is also a measure of whether a patient is in cardiopulmonary arrest or has loss of circulation or ventilation.

While blood pressure measurements are critical for determining chronic states of health as well as critical for measurements during code situations, presents methods of blood pressure measurement are typically as cumbersome and bulky as when it was first developed. Currently, blood pressure is typically measured using a stethoscope and sphygmomanometer. The sphygmomanometer cuff is inflated above the patient's systolic blood pressure to completely occlude the vessel, usually the brachial artery. The air in the sphygmomanometer cuff is then deflated, and the stethoscope is used to listen for the first sounds of turbulent flow after the vessel opens due to reduced pressure. That first sound is then recorded as the systolic pressure as the sound correlates to a cuff pressure.

The sounds of turbulent flow continue until the vessel is completely opened as the cuff is continuously deflated, leading eventually to completely linear flow when the vessel is completely opened. At this time, the loss of the turbulent blood flow, causes the Korotkov sounds (turbulent flow) to cease, and the pressure at which the sounds cease, is recorded as the patient's diastolic blood pressure. The systolic and diastolic pressures then are recorded as the patient's blood pressure. While this is the present "gold standard" for blood pressure measurement, it requires multiple pieces of equipment, and takes several minutes to configure equipment and take a measurement. In a cardiopulmonary arrest situation, where the blood pressure is critical in determining the patient's vital status, these minutes may be invaluable.

Additionally, blood pressure is dynamic and changes on a beat to beat and second by second basis. The conventional method of blood pressure measurement, described above, may not be capable of determining second to second measurement of blood pressure variation As such, current noninvasive blood pressure measurements are almost always conducted using a blood pressure cuff. While this apparatus is relatively simple and inexpensive, it has several limitations, including susceptibility to ambient noise, patient discomfort, and inability to obtain a continuous blood pressure measurement. It also requires that a clinician is constantly present to measure the blood pressure unless the automated oscillometric method is used; however, this automated method has its own limitations and has had some issues with accuracy. An alternative is invasive blood pressure measurement using an arterial catheter which is inserted into the radial or femoral artery. While this provides much higher quality data than an external cuff, its invasive nature also produces much higher risks, including infection, hemorrhage, or ischemia. Therefore, this method is only applied to critically ill patients and requires the presence of a trained medical doctor to perform. Alternative non-invasive modalities for measuring continuous blood pressure are highly desirable, particularly as hypertension has become an increasingly prevalent medical issue in countries throughout the world.

SUMMARY

Embodiments of the present disclosure are directed to a continuous blood pressure measurement device and methods of use thereof.

In one embodiment, a blood pressure measurement device comprises: a first transducer configured to emit multiple soundwaves having multiple frequencies, the soundwaves configured to cause a blood vessel of a subject to vibrate; a second transducer configured to capture one or more ultrasound images of the blood vessel; and a processing device configured to: determine, based on the one or more ultrasound images, a wall thickness, a radius, and a resonant frequency of the blood vessel; and calculate, based on the wall thickness, the radius, and the resonant frequency, a blood pressure of the subject.

In some implementations, the one or more ultrasound images comprise multiple ultrasound images, wherein determining the resonant frequency of the blood vessel, comprises: determining, based on the ultrasound images, a frequency of the multiple frequencies that maximized a vibration of the blood vessel; and selecting the frequency as the resonant frequency.

In some implementations, the blood pressure measurement device further comprises: an audio signal generator electrically coupled to the first transducer, the audio signal generator configured to adjust a frequency of sound waves emitted by the first transducer. In some implementations, the audio signal generator comprises at least one variable resistor that adjusts the frequency of sound waves emitted by the first transducer.

In some implementations, each of the frequencies is between 1 Hz and 3000 Hz. In some implementations, each of the frequencies is between 670 Hz and 2300 Hz.

In some implementations, the blood vessel is a carotid artery of the subject.

In some implementations, the first transducer is an audio speaker.

In some implementations, the blood pressure measurement device further comprises a substrate, the substrate comprising an adhesive surface for adhering to the subject's skin, wherein the first transducer and the second transducer are incorporated in the substrate.

In one embodiment, a non-transitory computer-readable storage medium stores instructions executable by a processor, wherein execution of the instructions cause a blood pressure measurement device to perform operations comprising: emitting, using a first transducer in proximity to a blood vessel of a subject, multiple soundwaves having multiple frequencies, the soundwaves causing a blood vessel of a subject to vibrate; determining, based on the vibrational response of the blood vessel to the soundwaves, a resonant frequency of the blood vessel; determining, using a second transducer that emits ultrasonic waves, a wall thickness and a radius of the blood vessel; and calculating, based on the resonant frequency, the wall thickness, and the radius, a blood pressure of the subject.

In some implementations, the operations further comprise: capturing, using the second transducer, multiple ultrasound images of the blood vessel when it vibrates in response to the soundwaves, wherein determining the resonant frequency of the blood vessel comprises: determining the resonant frequency of the blood vessel from the ultrasound images.

In some implementations, determining the wall thickness and the radius of the blood vessel, comprises: directing, using the second transducer, ultrasonic waves to the blood vessel; and receiving, using the second transducer, ultrasonic waves reflected from echogenic boundaries of the blood vessel.

In some implementations, after calculating the blood pressure, the operations further comprise: determining, using the first transducer and second transducer, an updated radius of the blood vessel and an updated velocity of blood flowing through the blood vessel; and calculating, based on the updated radius and the updated velocity, an updated blood pressure.

In one embodiment, a method comprises: emitting, using a first transducer in proximity to a blood vessel of a subject, multiple soundwaves having multiple frequencies, the soundwaves causing a blood vessel of a subject to vibrate; determining, based on the vibrational response of the blood vessel to the soundwaves, a resonant frequency of the blood vessel; determining, using a second transducer that emits ultrasonic waves, a wall thickness and a radius of the blood vessel; and calculating, based on the resonant frequency, the wall thickness, and the radius, a blood pressure of the subject.

In some implementations, the method further comprises: capturing, using the second transducer, multiple ultrasound images of the blood vessel when it vibrates in response to the soundwaves, wherein determining the resonant frequency of the blood vessel comprises: determining the resonant frequency of the blood vessel from the ultrasound images.

In some implementations, after calculating the blood pressure, the method further comprises: determining, using the first transducer and second transducer, an updated radius of the blood vessel and an updated velocity of blood flowing through the blood vessel; and calculating, based on the updated radius and the updated velocity, an updated blood pressure.

Other features and aspects of the disclosed technology will become apparent from the following detailed description, taken in conjunction with the accompanying drawings, which illustrate, by way of example, the features in accordance with implementations of the disclosed technology. The summary is not intended to limit the scope of any inventions described herein, which are defined by the claims and equivalents.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed.

DETAILED DESCRIPTION

Although some blood pressure measurement methods have demonstrated the use of ultrasound to measure relative changes in blood pressure as it varies over the course of a heartbeat, these methods are incapable of establishing a baseline diastolic pressure and therefore rely on initial calibration for each patient using another tool such as a pressure cuff or force probe. As such, measurement of an absolute blood pressure with these prior techniques requires the application of some form of external stimulus, such as a pressurized cuff or arterial line, in order to establish a baseline. These methods are unable to provide for the continuous measurement of blood pressure without performing a calibration step before the measurement.

Furthermore, to date, all attempts at measuring blood pressure waveforms using ultrasound have employed commercial ultrasound probes which use large arrays of piezoelectric or capacitive elements to form a cross-sectional image of the artery in question. The high cost of these machines has largely limited their deployment to hospitals that can afford to pay for both the instrument and a trained ultrasound technician capable of using it properly.

To address the aforementioned deficiencies of present techniques for measuring blood pressure, the technology disclosed herein is directed to a blood pressure measurement apparatus that enables continuous, non-invasive blood pressure measurement using sound and ultrasound transducers. In accordance with implementations of the disclosure, an electroacoustic transducer is used to generate an audio signal that stimulates vibrations in an artery. By varying the frequency of the acoustic signal, a resonant frequency at which the artery vibrates most strongly may be discovered/ estimated. This estimated resonant frequency may be combined with ultrasound measurements of the radius of the artery to calculate an absolute blood pressure. By virtue of using a device that applies acoustic stimulation to measure blood pressure, the need for a separate calibration step is obviated and blood pressure monitoring may be provided in an inexpensive and easy-to-use form.

Figure 1:
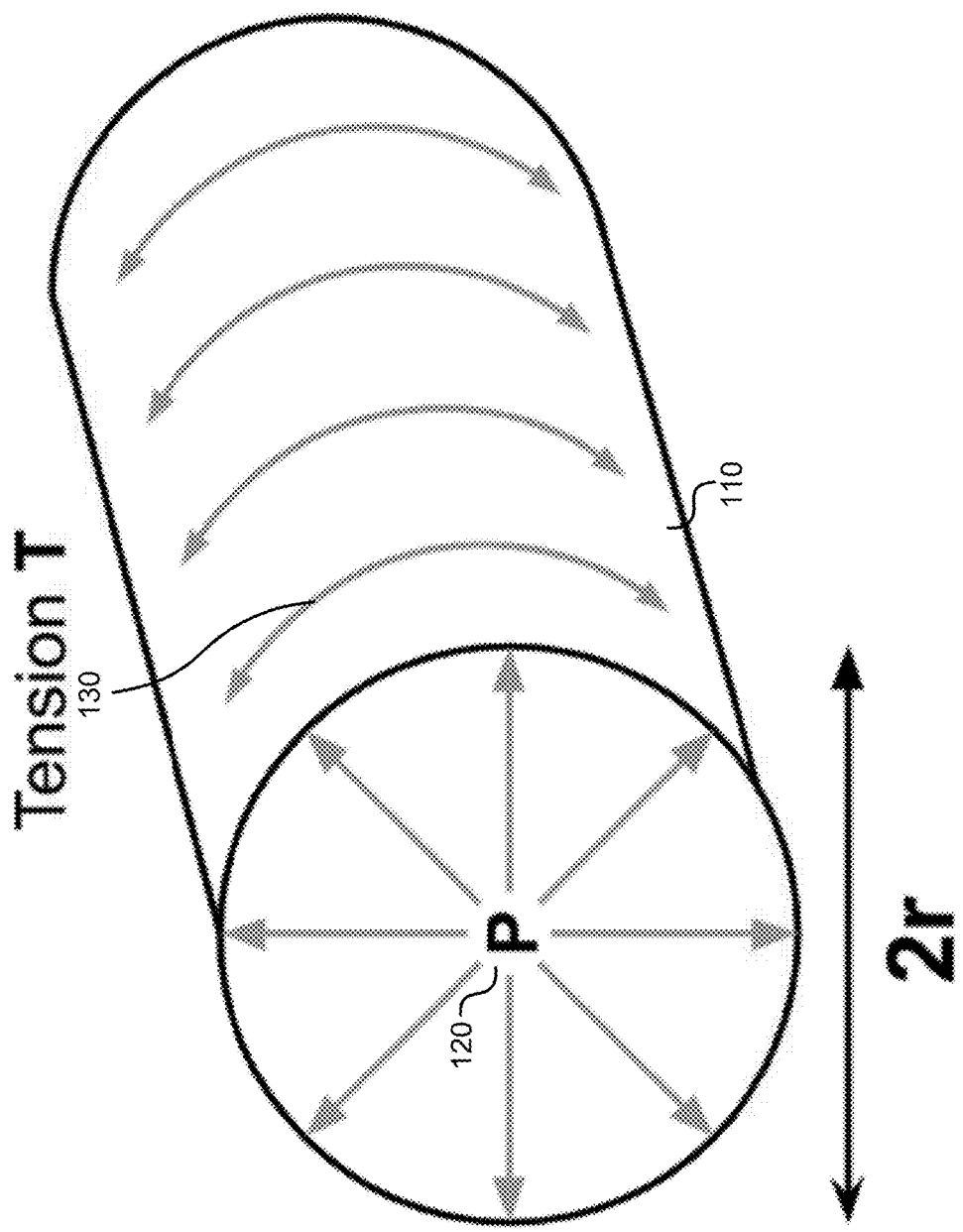
FIG. 1 depicts forces acting upon an arterial membrane, according to an embodiment.

To understand the principles underlying the technology described herein, it is instructive to consider the fluid dynamics underlying blood flow through an artery. To this end, FIG. 1 depicts an arterial wall 110, which essentially may be represented as a tube composed of elastic material. The dynamics of arterial wall 110 are dictated by the balance between blood pressure 120 pushing the wall out and tensile force 130 holding the wall together. Laplace's law states that for fluid flowing through a cylindrical elastic membrane with constant radius R, the fluid pressure P and the tensile force in the membrane T are related by the equation T=RP.

Figure 2:
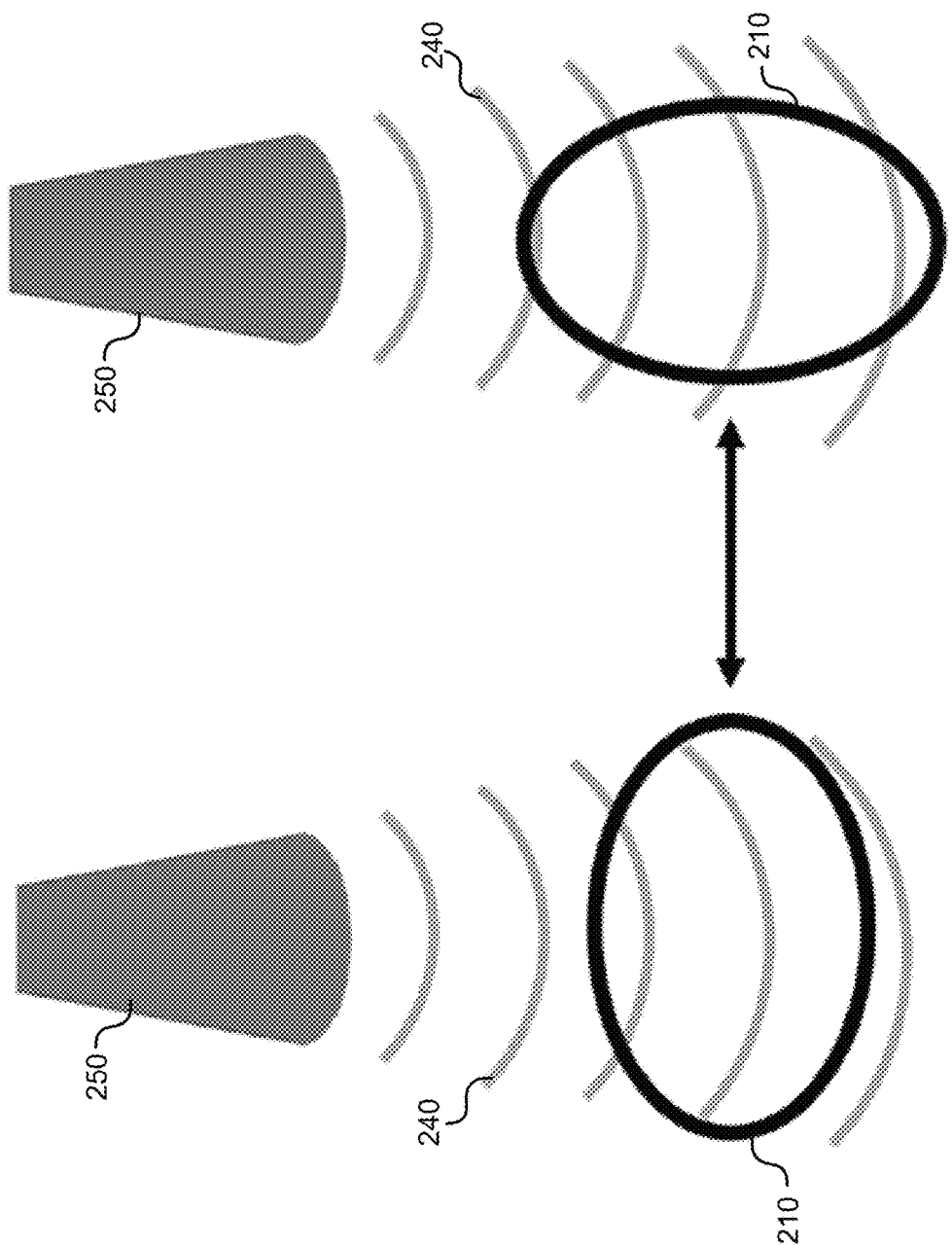
FIG. 2 depicts vibration of an arterial wall at different frequencies, in accordance with implementations of the disclosure.

The radius of the artery may be measured use one or more ultrasound sensors or transducers. As such, the remaining task for estimating the fluid pressure P is determining the tensile force T in the wall of the artery. In accordance with implementations of the disclosure, the tensile force may be estimated by measuring how the arterial wall responds to an impulse from an acoustic stimulus. FIG. 2 depicts this process. As shown, an acoustic stimulus 240, produced by an electroacoustic transducer 250, may be used to induce measurable perturbations in the arterial wall 210 while staying well below acoustic intensity limits specified by a health agency (e.g., U.S. FDA guidelines). By focusing on vibrational modes around the circumference of the artery, and particularly, the lowest-energy vibration which can be excited around the circumference, the tensile force may be estimated as follows.

The lowest-energy vibration has a wavelength of $\lambda=\pi R$. The mechanical properties of the arterial wall also dictate a speed, $v_w$, at which vibrations travel along the circumference of the wall. The wave speed and wavelength quantities combine to produce a resonant frequency $f=v_w/\lambda$. If an external stimulus (e.g., sound wave) is applied with resonant frequency f, the wall will vibrate very strongly, but if the frequency of the stimulus is varied away from f, the amplitude of the vibration will decrease. Thus, the resonant frequency f may be determined by applying an acoustic stimulus across a frequency range and finding the frequency at which the artery vibrates most strongly. This, in turn, may be used to determine the wave speed $v_w=\lambda f=\pi R f$. In an elastic material under tension, with volumetric density $\rho$ and thickness h, this wave speed is related to the tensile force via the equation $T=\rho h v_w^2$. The volumetric density of the arterial wall is nearly constant across patients, and the wall thickness may be measured from an ultrasound image in the same manner as R. Using this information, pressure may be determined based on Equation (1):

$$P=T/R=\rho h v_w^2/R=\pi^2 \rho h R f^2 \quad (1)$$

Accordingly, by measuring arterial wall thickness h and the radius of the artery R via ultrasound imaging, and by using an electroacoustic transducer in combination with ultrasonic imaging to estimate the resonant frequency f at which the artery vibrates most strongly, blood pressure may be calculated.

To illustrate the feasibility of the continuous blood pressure measurement techniques described herein, the following factors may be considered. First, to illustrate the practically of this blood pressure measurement method, it may be ensured that the resonant frequency, f, will take on a reasonable value in the typical patient. In a common carotid artery, the measurement quantities typically have values of about 100 mmHg for P, 2.5 mm for R, 0.3 mm for h, and 1 g/mL for $\rho$. Inserting these values into Equation (1) yields a predicted resonant frequency of approximately 1.3 kHz. Thus, in order to detect this vibration, sampling may need to be conducted at at least ~3 kHz in order to surpass the Nyquist rate. Currently available ultrasound instruments may produce imaging rates of at least 8 kHz, far surpassing the minimum sampling rate. 1.3 kHz is also far higher than the frequency of heartbeats, which in human patients does not exceed 5 Hz even under extreme conditions. Because resonant vibrations occur at a much higher frequency than the rate of change in pressure from the heartbeat, blood pressure (and thus the tensile force) may be assumed as constant over the duration of each vibrational cycle, substantially simplifying analysis. Furthermore, 1.3 kHz falls comfortably in the range of existing commercial speakers, so no specialized hardware is required to produce a tone with sufficient amplitude and frequency to stimulate arterial vibration.

Second, another measure of feasibility is the frequency range over which the electroacoustic transducer may need to operate. Under extreme conditions, a patient's blood pressure may be as low as 25 mmHg or as high as 300 mmHg. With the arterial dimensions given above, this corresponds to a resonant frequency range of 670 Hz to 2.3 kHz, still well within the acoustic range produced by commercial speakers.

Third, the level of frequency resolution required to obtain a useful level of precision in pressure measurements may also be considered. In order to be comparable to the current clinical gold standard of continuous blood pressure measurement, a blood pressure measurement device should be able to measure pressure to a precision of at least ±5 mmHg. With the arterial dimensions given above, a blood pressure swing of this magnitude would result in a change in the resonant frequency of ±34 Hz, or roughly 2.5%. This level of precision can also be readily obtained from commercially available speakers.

Figure 3:
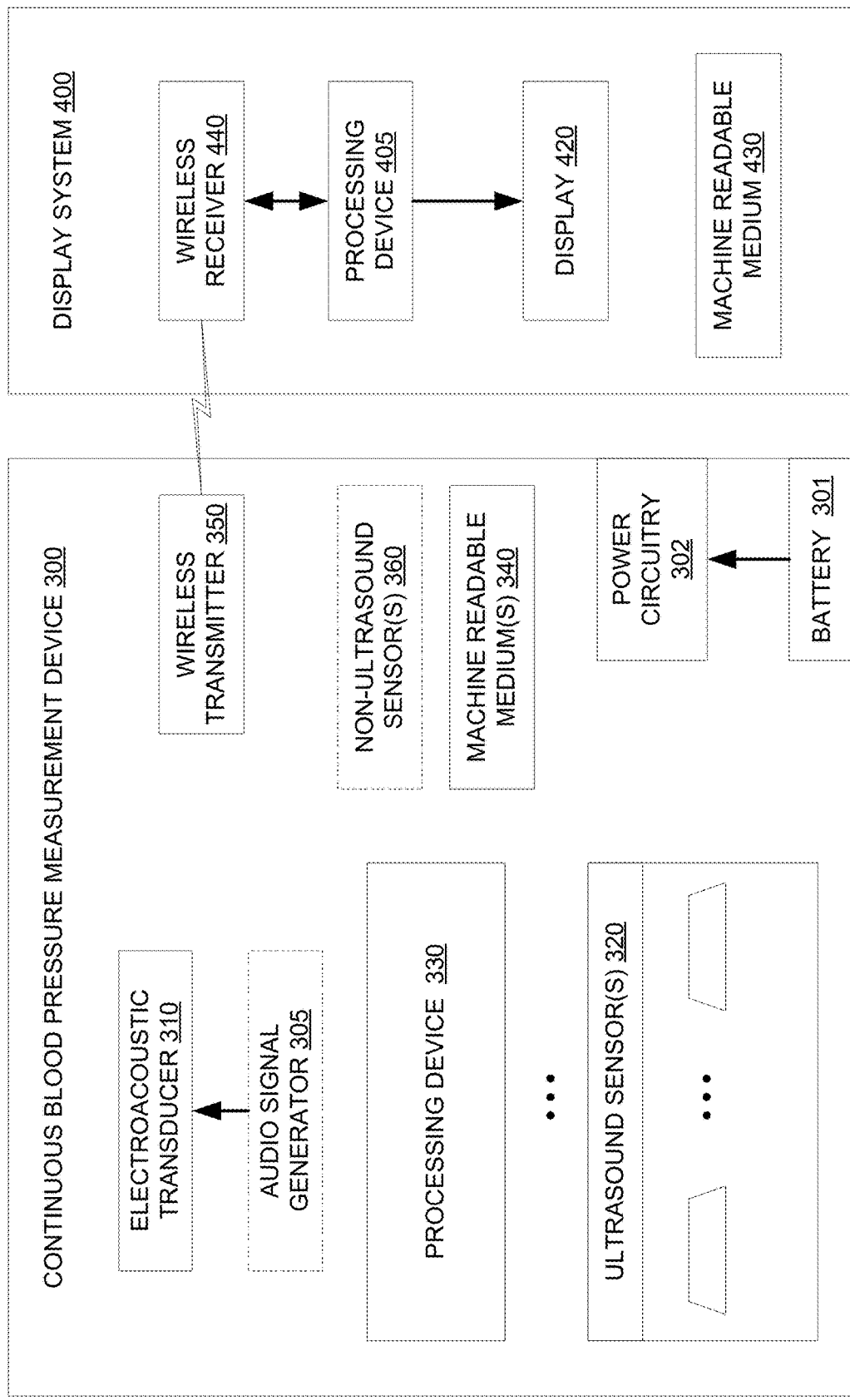
FIG. 3 depicts echogenic boundaries of an arterial wall, in accordance with implementations of the disclosure.

FIG. 3 is a block diagram illustrating some components of a continuous blood pressure measurement device 300, in accordance with implementations of the disclosure. As depicted, device 300 includes an audio signal generator 305, an electroacoustic transducer 310, at least one ultrasound sensor 320, at least one processing device 330, at least one machine readable medium 340, a wireless transmitter 350, and, optionally, one or more non-ultrasound sensor(s) 360. The electrical components of device 300 may be powered by a battery 301 that connects to power circuitry 302 for distributing power. The battery 301 may be rechargeable (e.g., via a USB port and/or an AC/DC converter). Although a battery 301 is shown in this example, it should be appreciated that any suitable battery or power supply technologies may be used to power the components of device 300. For example, lithium-ion batteries, cell batteries, piezo or vibration energy harvesters, photovoltaic cells, AC/DC sources, or other like devices can be used.

Electroacoustic transducer 310 may be implemented as an audio speaker that can output sound waves within a suitable range of frequencies (e.g., to find a resonant frequency of a blood vessel). For example, the speaker may be implemented as a bass speaker, a mid-range speaker, and/or a treble speaker (e.g., tweeter). In some implementations, a combination of speakers may be used to output sound within a suitable range of frequencies. An audio signal generator 305 that adjusts a frequency of sound waves may be coupled to transducer 310. In some implementations, the audio signal generator comprises at least a variable resistor that adjusts a frequency of the sound waves. The variable resistor may be a potentiometer. In some implementation, the blood pressure measurement device 300 may display the frequency of the sound waves. In some implementations, the audio signal generator 305 is a component of a processing device 330.

In some embodiments, the sound waves output by electroacoustic transducer 310 may be configured to be varied over a range of frequencies from about 100 Hz to about 3,500 Hz. In an embodiment, the range of frequencies the electroacoustic transducer 310 is varied over is about 100 Hz to about 500 Hz, about 100 Hz to about 1,000 Hz, about 100 Hz to about 1,500 Hz, about 100 Hz to about 2,000 Hz, about 100 Hz to about 2,500 Hz, about 100 Hz to about 3,000 Hz, about 100 Hz to about 3,500 Hz, about 500 Hz to about 1,000 Hz, about 500 Hz to about 1,500 Hz, about 500 Hz to about 2,000 Hz, about 500 Hz to about 2,500 Hz, about 500 Hz to about 3,000 Hz, about 500 Hz to about 3,500 Hz, about 1,000 Hz to about 1,500 Hz, about 1,000 Hz to about 2,000 Hz, about 1,000 Hz to about 2,500 Hz, about 1,000 Hz to about 3,000 Hz, about 1,000 Hz to about 3,500 Hz, about 1,500 Hz to about 2,000 Hz, about 1,500 Hz to about 2,500 Hz, about 1,500 Hz to about 3,000 Hz, about 1,500 Hz to about 3,500 Hz, about 2,000 Hz to about 2,500 Hz, about 2,000 Hz to about 3,000 Hz, about 2,000 Hz to about 3,500 Hz, about 2,500 Hz to about 3,000 Hz, about 2,500 Hz to about 3,500 Hz, or about 3,000 Hz to about 3,500 Hz. In an embodiment, the range of frequencies the electroacoustic transducer 310 is varied over is about 100 Hz, about 500 Hz, about 1,000 Hz, about 1,500 Hz, about 2,000 Hz, about 2,500 Hz, about 3,000 Hz, or about 3,500 Hz. In an embodiment, the range of frequencies the electroacoustic transducer 310 is varied over is at least about 100 Hz, about 500 Hz, about 1,000 Hz, about 1,500 Hz, about 2,000 Hz, about 2,500 Hz, or about 3,000 Hz. In an embodiment, the range of frequencies the electroacoustic transducer 310 is varied over is at most about 500 Hz, about 1,000 Hz, about 1,500 Hz, about 2,000 Hz, about 2,500 Hz, about 3,000 Hz, or about 3,500 Hz.

In some implementations, audio signal generator 305 may be configured to adjust the frequency of sound waves output by transducer 310 in suitable increments to search for the resonant frequency of vibration at a sufficient accuracy. For example, the frequency may be adjusted in increments between 1 Hz and 500 Hz such as 1 Hz, 5 Hz, 10 Hz, 25 Hz, 50 Hz, 100 Hz, 200 Hz, 500 Hz, etc. The accuracy of the estimated resonant frequency may be improved by decreasing the size of each increment. Conversely, the time it takes to estimate the resonant frequency may be improved by increasing the size of each increment.

The one or more ultrasound sensors 320 (individually referred to as "an ultrasound sensor 320") are configured to collect imaging data of a subject (e.g., blood vessel a subject). The imaging data may be used to measure the wall thickness of a blood vessel and the radius of the blood vessel. The blood vessel may be an artery or a vein. Additionally, the imaging data may be used to determine the resonant frequency of vibration of the blood vessel, which vibrates in response to the sound waves output by electroacoustic transducer 310. Each ultrasound sensor 320 includes a transducer configured to convert electricity to ultrasound and vice versa. For example, the transducer may be a piezoelectric transducer that oscillates and produces an ultrasonic pulse when an AC voltage is applied. Alternatively, the transducer may be a capacitive transducer that produces ultrasonic soundwaves using electrostatic fields between a conductive diaphragm and a backing plate. Ultrasound soundwaves may be produced at a frequency greater than or equal to about 20 kilohertz (KHz). In implementations, the transducer of an ultrasound sensor 320 may produce ultrasound in a frequency anywhere between 2 megahertz (MHz) and 20 MHz. When a reflected ultrasound signal (i.e., an "echo") is received by the transducer, an electrical signal may be generated and used by ultrasound sensor 120 to determine a distance to the imaged subject. In particular implementation, the transducer may produce ultrasound in a frequency between 7 MHz and 11 MHz.

Figure 4:
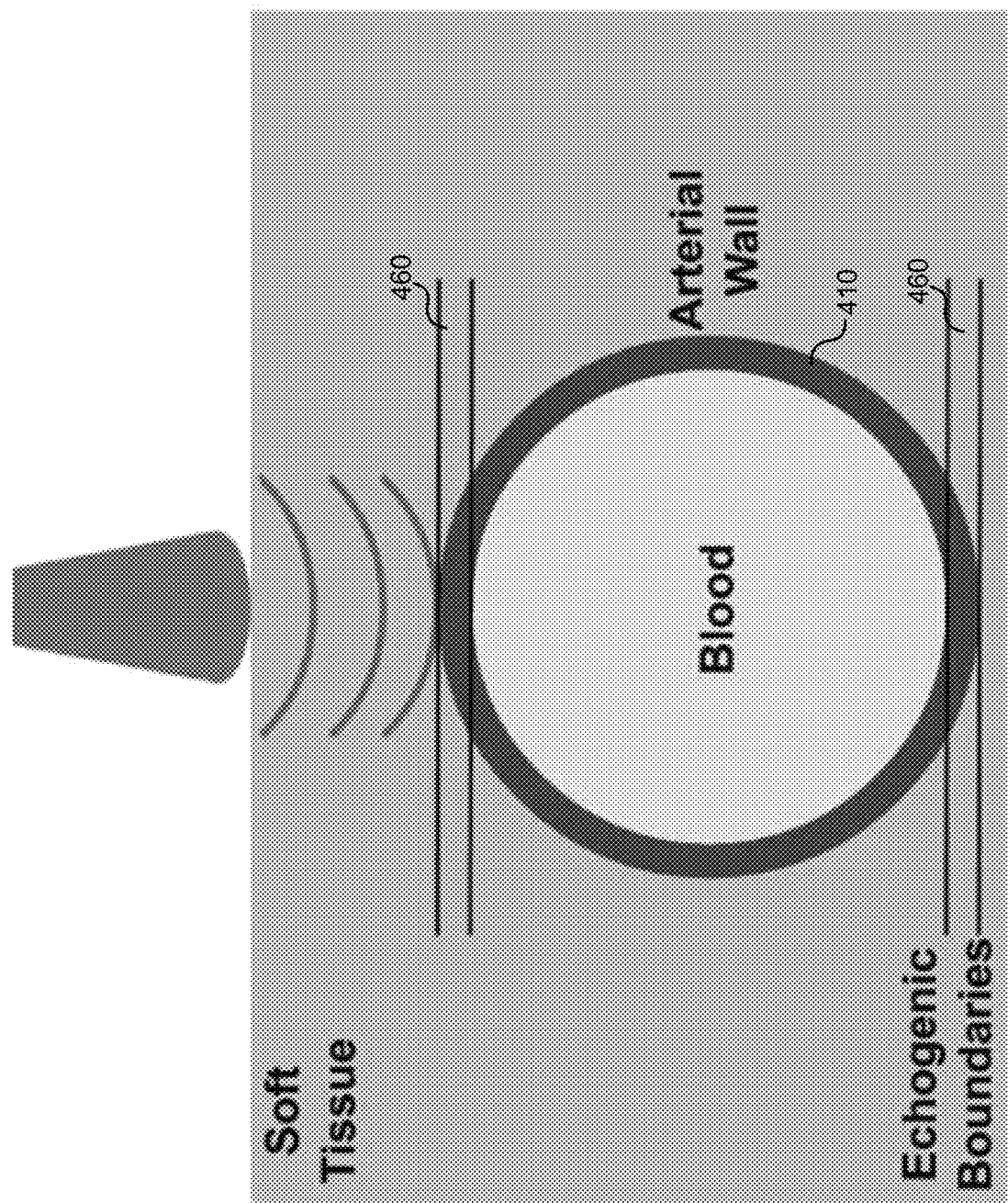
FIG. 4 is a block diagram illustrating some components of a continuous blood pressure measurement device, in accordance with implementations of the disclosure.

In one embodiment, ultrasonic measurement is performed using only a single piezoelectric element. Ultrasonic waves in the body are primarily reflected by sharp boundaries between regions of different densities. Many arteries, including the carotid, are embedded in soft tissue of relatively uniform density, so the only significant sources of echoes are the boundaries 460 formed by the inner and outer edges of the arterial wall 410 as depicted by FIG. 4. By measuring the delay between echoes received from these different boundaries, accurate determination of arterial radius and wall thickness from a single piezoelectric element is achievable.

As depicted in FIG. 2, when an acoustic stimulus 240 is applied to an artery (e.g., using a tweeter), the resulting vibration will cause the arterial diameter, observed using ultrasound imaging, to oscillate sinusoidally as the axis perpendicular to the incident sound waves expands and contracts. If the power of the stimulus is kept constant this oscillation will have maximum amplitude when the stimulus is applied at a frequency matching the resonant frequency of the arterial wall 210. Thus, the resonant frequency may be determined by applying the acoustic stimulus at a range of different frequencies and determining, via ultrasound imaging, the point at which the observed amplitude of oscillation is at a maximum. With this setup, the velocity of the wall may also be determined independently of its position by measuring the Doppler shift of the returned echo. Since wall velocity will also be maximized at resonance, the velocity measurement will give an orthogonal means of determining the resonance point and thereby increase precision.

In a further embodiment, precision may be increased by increasing the number of ultrasonic piezoelectric elements. In one implementation, four piezoelectric elements may be utilized. One of the piezoelectric elements could produce an ultrasonic signal while the other three listen for echoes, allowing for triangulation of echoes as they are received. This embodiment may allow for better exclusion of spurious echoes and thereby provide better isolation of echoes being produced by the arterial wall.

Ultrasound that enters tissue may be transmitted, attenuated or reflected. While higher frequency ultrasound may provide for a higher resolution signal, it may provide poor depth penetration of imaged tissue. Conversely, while lower frequency ultrasound may provide for a lower resolution signal, it may provide better depth penetration of imaged tissue. To overcome these limitations, some implementations may use multiple ultrasound sensors 320, with each ultrasound sensor 320 having a transducer configured with a unique resonance frequency. Specifically, the ultrasound transducers may be selected such that their acoustic frequency responses are non-overlapping. By actuating the transducers in a time interleaved fashion, each sensor may be used to image a surface of a sample at a unique depth. Furthermore, each transducer may be simultaneously actuated with a combination of other transducers to generate higher order harmonics that allow for sub-pixel feature resolution. In some implementations, ultrasound sensor transducers may be selected that are adjacent and partially overlapping in frequency response, allowing for the normalization of the measurement of any pair of sensors, thereby reducing systemic sources of noise and significantly increasing signal integrity. Additionally, the simultaneous interrogation of a surface with transducers with distinct resonance frequencies may be used to generate super-resolution ultrasound images. In such implementations, the frequency overlap between sensors may be configured to be about 200 KHz or less. In implementations, the frequency overlap between sensors may be configured such that a frequency response range of one ultrasound sensor does not overlap with a resonant frequency of another ultrasound sensor, where the resonant frequency of the ultrasound sensor may refer to an operating frequency at which the transducer most efficiently converts electrical energy into mechanical energy.

Processing device 330 may be configured to control operation of the components of device 300, including audio signal generator 305 (which in some embodiments is a component of processing device 130), electroacoustic transducer 310, ultrasound sensor(s) 320, and non-ultrasound sensor(s) 360 (further discussed below). For example, processing device 330 may be configured to cause electroacoustic transducer 310 to emit sound at a specific frequency or range of frequencies. Additionally, processing device 330 may configured to cause ultrasound sensors 320 and/or non-ultrasound sensor(s) 360 to perform image acquisition. Furthermore, processing device 330 may receive, store (e.g., in machine readable medium 340), and/or process signal measurements received from ultrasound sensors 320 and/or non-ultrasound sensors 360. In some implementations, processing device 330 may also be configured to use signal measurements received from ultrasound sensors 320 to continuously measure blood pressure of an artery or other blood vessel. The aforementioned methods may be applied by processing device 330 by executing instructions stored on a machine readable medium 340. In one embodiment, processing device 330 may be implemented as a single integrated circuit (IC) microcontroller that includes memory (e.g., machine readable medium 340) for storing program information and data.

As described above, continuous blood pressure measurement device 300 may accurately determine blood pressure solely from arterial radius, wall thickness, and resonant frequency. However, those three values are not the only information that may be determined. In some implementations, in the course of measuring the vibrational response of the artery under a range of frequencies, additional information may be obtained, including: the strength and width of the resonance peak, the baseline excitation level at low frequencies, and/or the level of excitation of higher-energy vibrational modes. Changes in these parameters may also be observed over the course of a heartbeat as blood pressure and tension levels change. Ultrasound imaging of the artery may also yield information about the echogenicity of the arterial wall, which may provide insight into levels of calcification and plaque buildup. All the additional information may be used to refine calculations, attain better precision, and/or provide additional information about the patient's overall health.

In some implementations, continuous blood pressure measurement device 300 may include one or more non-ultrasound sensors 360 to allow for multi-modal measurement of other health indicators besides blood pressure. For example, LED light sources and photodiode receivers may be integrated onto the wireless platform to measure blood oxygenation through pulse oximetry. Other example sensors that may be implemented include sensors for detecting body fluid status, ejection fraction of the heart, or other vital measurements may be integrated into the hardware/sensor package. In some implementations, the measurements made using non-ultrasound sensors 360 may be correlated and normalized with ultrasound measurements used to calculate blood pressure. By virtue of using additional modalities besides ultrasound sensors 320 to measure blood pressure, the accuracy of device 300 may be improved.

In the example, of FIG. 3, continuous blood pressure measurement device 300 includes a wireless transmitter 350 (e.g., transceiver) that is configured to communicate ultrasound measurement data to wireless receiver 440 (e.g., transceiver) of display system 400. Depending on the ultrasound imaging application, the received ultrasound measurement data may be processed using processing device 405 of display system 440 (e.g., into a format appropriate for display) and/or displayed using display 420. For example, the display 420 may be a component of a cardiac monitor, a mobile device (e.g., smartphone or head mounted display), or some other suitable display device. The display 420 may also display the frequency of sound waves electroacoustic transducer 310 is configured to emit (e.g., via audio signal generator 305). The wireless communication link between wireless transmitter 350 and wireless receiver 440 may be a radio frequency link such as a Bluetooth® or Bluetooth® low energy (LE) link, a Wi-Fi® link, a ZigBee link, or some other suitable wireless communication link. In other implementations, data transfer between device 300 and display system 400 may be achieved using a wired transmitter or other suitable wired interface. For example, data may be transferred using a USB-C connector, a USB 2.x or 3.x connector, a micro-USB connector, a THUNDERBOLT connector, an Ethernet cable, etc.

In alternative implementations, display 420 and/or the functions of display system 400 may be integrated into continuous blood pressure measurement device 300. In such implementations, continuous blood pressure measurement device 300 may still retain transmitter 350 to communicate historical or current blood pressure measurement data to an external device such as a smartphone.

Figure 5:
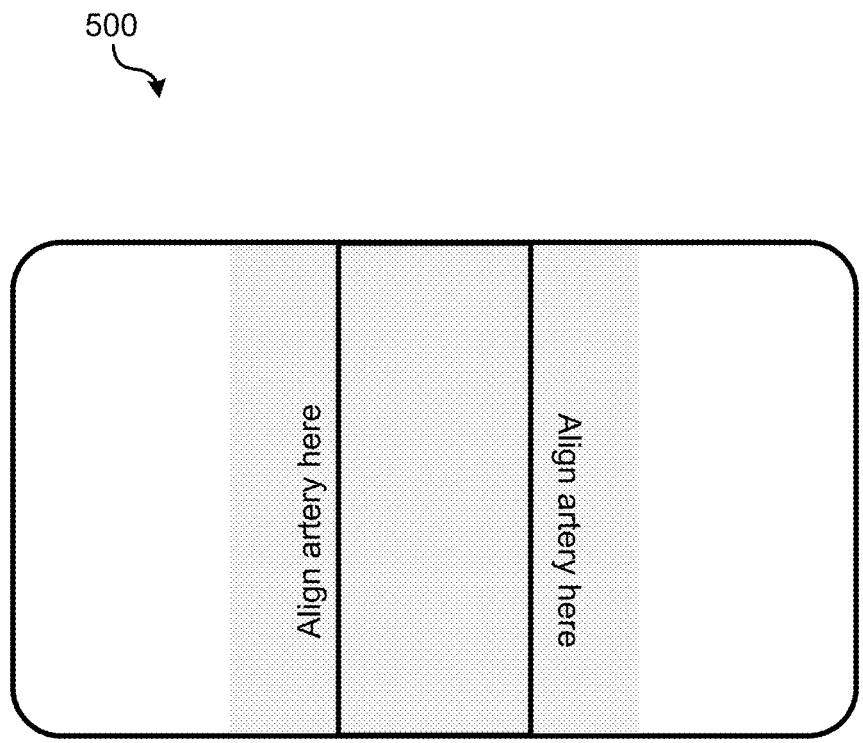
FIG. 5 illustrates an adhesive substrate including an integrated continuous blood pressure measurement device, in accordance with implementations of the disclosure.

In some implementations, depicted by FIG. 5, continuous blood pressure measurement device 300 may be incorporated into an adhesive substrate 500. As illustrated, substrate 500 includes one or more alignment lines or other markings for aligning the electroacoustic transducer 310 and one or more ultrasound sensors 320 of the device 300 with an artery of a patient prior to taking actuating transducer 310 and taking ultrasound measurements. Additionally, substrate 500 includes an adhesive (e.g., a rubber, acrylic, or acrlyic blend adhesive) on the back that may be used to hold substrate in place and in alignment with the patient's artery. During application, the adhesive may be exposed by peeling away a paper backing. For example, the device can be placed on the patient's neck to measure blood pressure through the carotid artery. Similar measurements may be made on the radial or ulnar arteries. By virtue of this implementation, the measurement of blood pressure may be noninvasive, reliable, fast, and provide continuous measurement, thus taking into account beat to beat variation. These continuous variations may be presented to a user on a display system 400 as described above.

Figure 6:
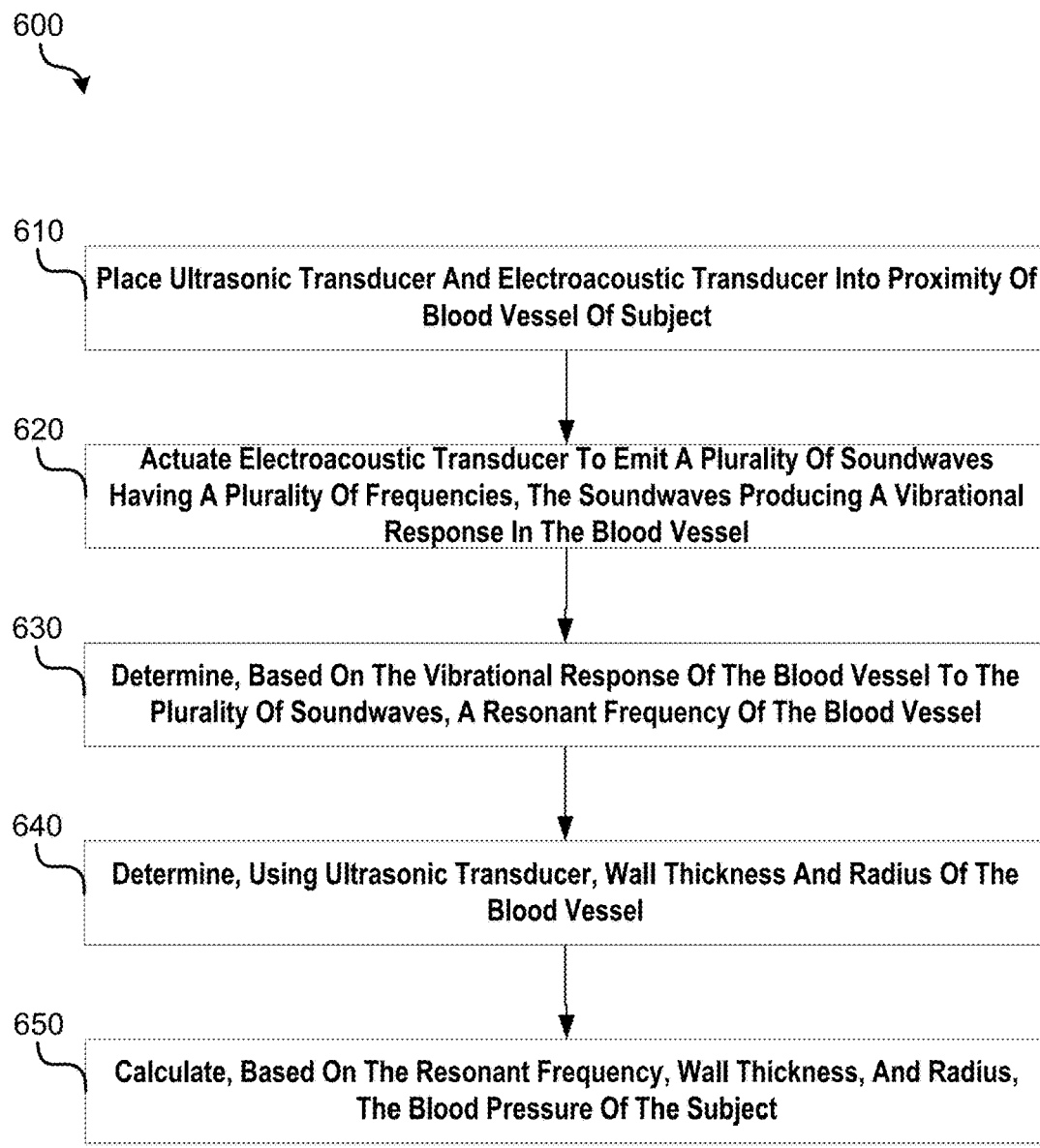
FIG. 6 is an operational flow diagram illustrating an example method for measuring blood pressure of a subject, in accordance with implementations of the disclosure.

FIG. 6 is an operational flow diagram illustrating an example method 600 for measuring blood pressure of a subject, in accordance with implementations of the disclosure. In some implementations, method 600 may be implemented using a continuous blood pressure measurement device 300 as described above.

At operation 610, an ultrasound transducer and electroacoustic transducer are brought into proximity of a blood vessel of the subject. For example, a continuous blood pressure measurement device 300 including an electroacoustic transducer 310 and ultrasound sensor 320 may be brought into proximity of an artery (e.g., carotid artery or brachial artery) of the patient. In a particular implementation, a substrate 500 including device 300 may be aligned with the subject's artery and subsequently adhered. For example, the substrate 500 may be adhered to the patient's arm in proximity to the brachial artery. Alternatively, the substrate may be adhered to the patient's neck in proximity to the carotid artery. In some implementations, the position of the ultrasound transducer and electroacoustic transducer (e.g., device 300 or substrate 500) may be adjusted to maximize the amplitude and/or signal-to-noise ratio of measurement signals.

At operation 620, the electroacoustic transducer is actuated to emit a plurality of soundwaves having a plurality of frequencies. For example, audio signal generator 305 may be configured to cause electroacoustic transducer 310 to emit sound waves at a plurality of different frequencies. The sound waves may produce a vibrational response in blood vessel (e.g., in a cross section of the blood vessel that the sound waves are directed to). The vibrational response may have an amplitude that varies depending on the frequency of the sound waves.

In some implementations, the frequency of each of the sound waves may be between 1 Hz and 3000 Hz. In some implementations, the frequency of each of the sound waves may be between 670 Hz and 2300 Hz.

At operation 630, based on the vibrational response of the blood vessel to the soundwaves at each of the plurality of different frequencies, the resonant frequency of vibration of the blood vessel may be determined (e.g., based on the frequency that produced the greatest amplitude of response). In some implementations, the resonant frequency may be held for a moment and then recorded in memory (e.g., in computer readable medium 340).

In some implementations, an ultrasonic sensor is used to detect the resonant frequency by capturing images of the blood vessel (e.g., the cross section) as it vibrates in response to different applied frequencies. The frequency that produces the highest amplitude of vibration may be selected (e.g., by a processing device communicatively coupled to the sensor) as the resonant frequency. In some implementations, the ultrasonic transducer has a sampling rate of at least 3 kHz.

In some implementations, the electroacoustic transducer and ultrasonic sensor may be placed adjacent one another and driven in synchronization. For example, a small speaker may be placed on either side of the ultrasonic sensor, and the two devices/components may be synchronously driven.

In particular implementations of operations 620 and 630, to improve the speed of finding the resonant frequency, an optimized search algorithm may be used to adjust the frequency of soundwaves output by the electroacoustic transducer in-between measurements. The search algorithm may utilize suitable boundary conditions (e.g., maximum frequency, minimum frequency, rate of frequency adjustment, etc.). The search algorithm may begin with a wide frequency scan over a large frequency range that uses large changes of frequency between measurements to find a narrower frequency range within which the resonant peak lies, and then transition to a narrow frequency scan within this narrower frequency range to find the resonant frequency. In some implementations, the resonant frequency may be held for a moment and then recorded in memory (e.g., in computer readable medium 340).

At operation 640, the wall thickness and radius of the blood vessel (e.g., for the cross section) are determined. These parameters may be determined from the ultrasound images captured using an ultrasound sensor 320. For example, echo-mode ultrasonography may be utilized to determine the wall thickness and radius. Ultrasonic waves may be directed to the blood vessel and ultrasonic waves reflected from echogenic boundaries of the blood vessel may be received. A doppler shift of the reflected ultrasonic waves may be measured using the ultrasonic sensor, and a wave velocity of the blood vessel may be calculated based on this doppler shift. In some implementations, multiple ultrasonic transducers may be utilized to improve imaging accuracy and/or speed. For example, one transducer could produce an ultrasonic signal while three others listen for echoes, allowing for triangulation of echoes as they are received.

At operation 650, the blood pressure is calculated based on the resonant frequency, the wall thickness, and the radius. The calculated blood pressure may establish a baseline diastolic pressure. Once an absolute diastolic pressure is established, changes in blood pressure over time (e.g., using doppler ultrasound imaging) may be measured with the ultrasound sensor(s) to extract a continuous waveform. When employing this type of differential measurement, a small but persistent inaccuracy aggregate into a large drift over the course of many heartbeats. Thus, periodic re-baselining may be required to maintain accuracy for a patient under long-term monitoring. This demonstrates another advantage of the proposed method; while other baselining techniques would require repeated application of an external pressure cuff or force probe, using the method herein, the baselining can be performed automatically at regular intervals using the electroacoustic transducer and the same ultrasonic hardware being employed to perform the continuous monitoring.

In some implementations, device 300 or an external display system 400 may display the computed blood pressure over time. In various implementations, a processing device 330 of continuous blood pressure measurement device 300 may perform the necessary DSP and calculations to arrive at the patient's blood pressure.

In alternative implementations, the electroacoustic transducer may be omitted and the acoustic signals of varying frequencies may be generated by pulsing the ultrasonic sensor at varying frequencies to deliver the energy to the blood vessel. This alternative design may have the advantage of using a single sensor to produce both the resonant response and capture ultrasound imaging data.

Figure 7:
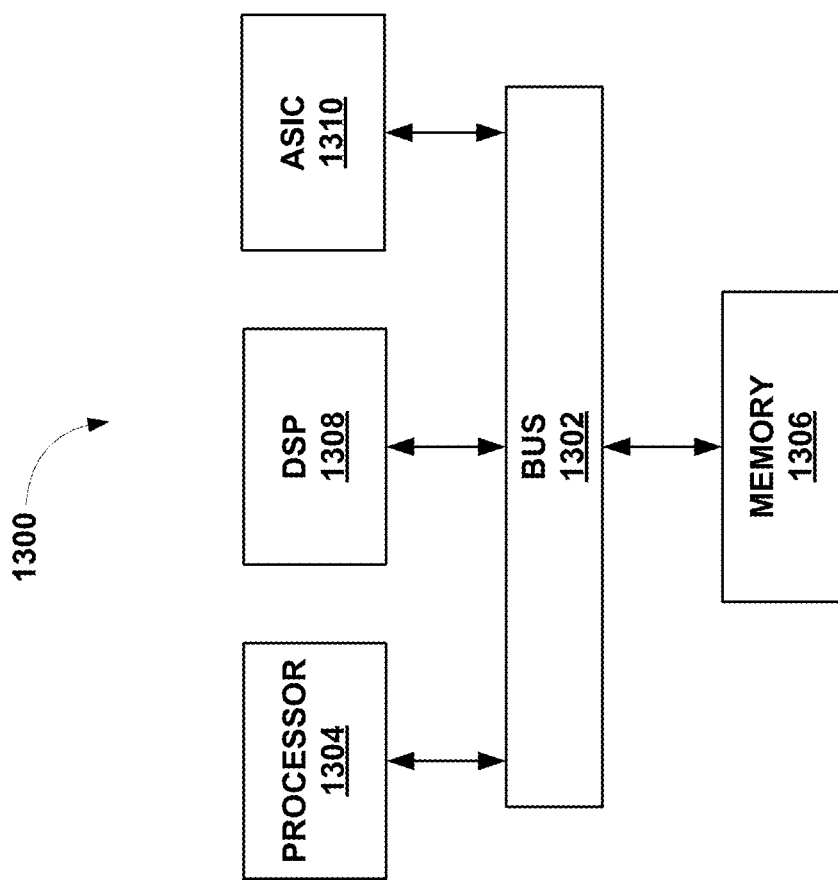
FIG. 7 illustrates an example chip set that can be utilized in implementing architectures and methods in accordance with various implementations of the disclosure.

FIG. 7 illustrates a chip set 1300 in which embodiments of the disclosure may be implemented. Chip set 1300 can include, for instance, processor and memory components incorporated in one or more physical packages. By way of example, a physical package includes an arrangement of one or more materials, components, and/or wires on a structural assembly (e.g., a baseboard) to provide one or more characteristics such as physical strength, conservation of size, and/or limitation of electrical interaction.

In one embodiment, chip set 1300 includes a communication mechanism such as a bus 1302 for passing information among the components of the chip set 1300. A processor 1304 has connectivity to bus 1302 to execute instructions and process information stored in a memory 1306. Processor 1304 includes one or more processing cores with each core configured to perform independently. A multi-core processor enables multiprocessing within a single physical package.

Examples of a multi-core processor include two, four, eight, or greater numbers of processing cores. Alternatively or in addition, processor 1304 includes one or more microprocessors configured in tandem via bus 1302 to enable independent execution of instructions, pipelining, and multithreading. Processor 1304 may also be accompanied with one or more specialized components to perform certain processing functions and tasks such as one or more digital signal processors (DSP) 1308, and/or one or more application-specific integrated circuits (ASIC) 1310. DSP 1308 can typically be configured to process real-world signals (e.g., sound) in real time independently of processor 1304. Similarly, ASIC 1310 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

Processor 1304 and accompanying components have connectivity to the memory 1306 via bus 1302. Memory 1306 includes both dynamic memory (e.g., RAM) and static memory (e.g., ROM) for storing executable instructions that, when executed by processor 1304, DSP 1308, and/or ASIC 1310, perform the process of example embodiments as described herein. Memory 1306 also stores the data associated with or generated by the execution of the process.

In this document, the terms "machine readable medium," "computer readable medium," and similar terms are used to generally refer to non-transitory mediums, volatile or non-volatile, that store data and/or instructions that cause a machine to operate in a specific fashion. Common forms of machine readable media include, for example, a hard disk, solid state drive, magnetic tape, or any other magnetic data storage medium, an optical disc or any other optical data storage medium, any physical medium with patterns of holes, a RAM, a PROM, EPROM, a FLASH-EPROM, NVRAM, any other memory chip or cartridge, and networked versions of the same.

These and other various forms of computer readable media may be involved in carrying one or more sequences of one or more instructions to a processing device for execution. Such instructions embodied on the medium, are generally referred to as "instructions" or "code." Instructions may be grouped in the form of computer programs or other groupings. When executed, such instructions may enable a processing device to perform features or functions of the present application as discussed herein.

In this document, a "processing device" may be implemented as a single processor that performs processing operations or a combination of specialized and/or general-purpose processors that perform processing operations. A processing device may include a CPU, GPU, APU, DSP, FPGA, ASIC, SOC, and/or other processing circuitry.

The various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

Each of the processes, methods, and algorithms described in the preceding sections may be embodied in, and fully or partially automated by, code components executed by one or more computer systems or computer processors comprising computer hardware. The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. Additionally, unless the context dictates otherwise, the methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A blood pressure measurement device, comprising:
    an electroacoustic transducer configured to emit multiple soundwaves having multiple frequencies, the soundwaves configured to cause a blood vessel of a subject to vibrate;
    an ultrasound transducer configured to capture multiple ultrasound images of the blood vessel, the multiple ultrasound images comprising a first set of images showing a vibrational response of the blood vessel to a first set of soundwaves emitted by the electroacoustic transducer over a first range of frequencies, and a second set of images showing a vibrational response of the blood vessel to a second set of soundwaves emitted by the electroacoustic transducer over a second range of frequencies narrower than the first range of frequencies; and
    a processing device configured to:
        determine, based on the multiple ultrasound images, a wall thickness, a radius, and a resonant frequency of the blood vessel; and
        calculate, based on the wall thickness, the radius, and the resonant frequency, a blood pressure of the subject, wherein determining the resonant frequency of the blood vessel comprises:
adjusting, based on the vibrational response of the blood vessel to the first set of soundwaves emitted by the electroacoustic transducer over the first range of frequencies, a frequency of soundwaves output by the electroacoustic transducer to emit the second set of soundwaves over the second range of frequencies;
determining, from the multiple ultrasound images, based on a vibrational response of the blood vessel to the soundwaves, a frequency of the multiple frequencies that maximizes a vibration of the blood vessel; and
selecting the frequency as the resonant frequency.

2. The blood pressure measurement device of claim 1, further comprising: an audio signal generator electrically coupled to the electroacoustic transducer, the audio signal generator configured to cause the multiple sound waves to have the multiple frequencies.

3. The blood pressure measurement device of claim 2, wherein the audio signal generator comprises at least one variable resistor that adjusts the multiple frequencies.

4. The blood pressure measurement device of claim 1, wherein each of the frequencies is between 1 Hz and 3000 Hz.

5. The blood pressure measurement device of claim 4, wherein each of the frequencies is between 670 Hz and 2300 Hz.

6. The blood pressure measurement device of claim 1, wherein the blood vessel is a carotid artery of the subject.

7. The blood pressure measurement device of claim 1, further comprising: a substrate, wherein the substrate comprises an adhesive surface for adhering to skin of the subject, wherein the electroacoustic transducer and the ultrasound transducer are incorporated in the substrate.

8. A blood pressure measurement device, comprising:
an electroacoustic transducer;
an ultrasound transducer;
a processor; and
a non-transitory computer-readable storage medium storing instructions executable by the processor, wherein execution of the instructions cause the blood pressure measurement device to perform operations comprising:
emitting, using the electroacoustic transducer in proximity to a blood vessel of a subject, multiple soundwaves having multiple frequencies, the soundwaves causing the blood vessel to vibrate;
capturing, using the ultrasound transducer, multiple ultrasound images of the blood vessel when the blood vessel vibrates in response to the soundwaves, the multiple ultrasound images comprising a first set of images showing a vibrational response of the blood vessel to a first set of soundwaves emitted by the electroacoustic transducer over a first range of frequencies, and a second set of images showing a vibrational response of the blood vessel to a second set of soundwaves emitted by the electroacoustic transducer over a second range of frequencies narrower than the first range of frequencies;
determining, from the multiple ultrasound images, based on a vibrational response of the blood vessel to the soundwaves, a resonant frequency of the blood vessel;
determining, using the ultrasound transducer, a wall thickness and a radius of the blood vessel; and
calculating, based on the resonant frequency, the wall thickness, and the radius, a blood pressure of the subject,
wherein determining the resonant frequency of the blood vessel comprises: adjusting, based on the vibrational response of the blood vessel to the first set of soundwaves emitted by the electroacoustic transducer over the first range of frequencies, a frequency of soundwaves output by the electroacoustic transducer to emit the second set of soundwaves over the second range of frequencies.

9. The blood pressure measurement device of claim 8, wherein determining the wall thickness and the radius of the blood vessel, comprises:
also directing, using the ultrasound transducer, ultrasonic waves to the blood vessel; and
also receiving, using the ultrasound transducer, ultrasonic waves reflected from echogenic boundaries of the blood vessel.

10. The blood pressure measurement device of claim 8, wherein after calculating the blood pressure, the operations further comprise:
determining, using the electroacoustic transducer and the ultrasound transducer, an updated radius of the blood vessel and an updated velocity of blood flowing through the blood vessel; and
calculating, based on the updated radius and the updated velocity, an updated blood pressure.

11. The blood pressure measurement device of claim 8, wherein each of the frequencies is between 670 Hz and 2300 Hz.

12. The blood pressure measurement device of claim 8, wherein the electroacoustic transducer is an audio speaker.

13. A method, comprising:
emitting, using an electroacoustic transducer in proximity to a blood vessel of a subject, multiple soundwaves having multiple frequencies, the soundwaves causing the blood vessel to vibrate;
capturing, using an ultrasound transducer, multiple ultrasound images of the blood vessel when the blood vessel vibrates in response to the soundwaves, the multiple ultrasound images comprising a first set of images showing a vibrational response of the blood vessel to a first set of soundwaves emitted by the electroacoustic transducer over a first range of frequencies, and a second set of images showing a vibrational response of the blood vessel to a second set of soundwaves emitted by the electroacoustic transducer over a second range of frequencies narrower than the first range of frequencies;
determining, from the multiple ultrasound images, based on a vibrational response of the blood vessel to the soundwaves, a resonant frequency of the blood vessel;
determining, using the ultrasound transducer, a wall thickness and a radius of the blood vessel; and
calculating, based on the resonant frequency, the wall thickness, and the radius, a blood pressure of the subject,
wherein determining the resonant frequency of the blood vessel comprises: adjusting, based on the vibrational response of the blood vessel to the first set of soundwaves emitted by the electroacoustic transducer over the first range of frequencies, a frequency of soundwaves output by the electroacoustic transducer to emit the second set of soundwaves over the second range of frequencies.

14. The method of claim 13, wherein determining the wall thickness and the radius of the blood vessel, comprises:
   also directing, using the ultrasound transducer, ultrasonic waves to the blood vessel; and
   also receiving, using the ultrasound transducer, ultrasonic waves reflected from echogenic boundaries of the blood vessel.

15. The method of claim 13, wherein after calculating the blood pressure, the method further comprises:
   determining, using the electroacoustic transducer and the ultrasound transducer, an updated radius of the blood vessel and an updated velocity of blood flowing through the blood vessel; and
   calculating, based on the updated radius and the updated velocity, an updated blood pressure.

16. The method of claim 13, wherein each of the frequencies is between 670 Hz and 2300 Hz.

17. The blood pressure measurement device of claim 1, wherein:
   the blood pressure is a diastolic blood pressure; and
   the processing device is further configured to: after calculating the diastolic blood pressure, continuously calculating, using the ultrasound transducer, changes in the diastolic blood pressure over time.

18. The blood pressure measurement device of claim 17, wherein the processing device is further configured to: after continuously calculating the changes in the diastolic blood pressure over time, recalculating, using the electroacoustic transducer and the ultrasound transducer, the diastolic blood pressure.

19. The blood pressure measurement device of claim 1, wherein calculating the blood pressure of the subject comprises: calculating the blood pressure of the subject as a function of the wall thickness, the radius, and the resonant frequency squared.

* * * * *